United States Patent [19]

Arnold, Jr. et al.

[11] Patent Number: 5,639,604
[45] Date of Patent: Jun. 17, 1997

[54] HOMOGENEOUS PROTECTION ASSAY

[75] Inventors: Lyle J. Arnold, Jr.; Norman C. Nelson, both of San Diego, Calif.

[73] Assignee: Gen-Probe Incorporated, San Diego, Calif.

[21] Appl. No.: 161,706

[22] Filed: Dec. 3, 1993

Related U.S. Application Data

[63] Continuation-in-part of Ser. No. 99,392, Sep. 21, 1987, abandoned, and a continuation of Ser. No. 613,603, Nov. 8, 1990, Pat. No. 5,283,174, which is a continuation of Ser. No. 294,700, Dec. 12, 1988, abandoned.

[51] Int. Cl.[6] .............. C07H 21/04; C12Q 1/00; C12Q 1/68
[52] U.S. Cl. .............. 435/6; 435/4; 435/7.1; 436/546; 536/25.32; 935/77; 935/78
[58] Field of Search .............. 435/6, 4, 7.1; 536/25.32; 935/77, 78; 436/546

[56] References Cited

U.S. PATENT DOCUMENTS

| | | | |
|---|---|---|---|
| 4,018,530 | 4/1977 | Hirschfeld | 356/317 |
| 4,358,535 | 11/1982 | Falkow et al. | 435/5 |
| 4,383,031 | 5/1983 | Boguslaski et al. | 435/7.72 |
| 4,558,014 | 12/1985 | Hirschfeld et al. | 436/527 |
| 4,581,333 | 4/1986 | Kourilsky et al. | 435/6 |
| 4,737,454 | 4/1988 | Dattagupta et al. | 536/24.31 |
| 5,283,174 | 2/1994 | Arnold, Jr. | 435/6 |

FOREIGN PATENT DOCUMENTS

| | | |
|---|---|---|
| 4031085 | 3/1984 | Australia . |
| 5214686 | 1/1985 | Australia . |
| 4018885 | 3/1985 | Australia . |
| 0082636 | 6/1983 | European Pat. Off. . |
| 0119448 | 9/1984 | European Pat. Off. . |
| 0164054 | 5/1985 | European Pat. Off. . |
| 0212951 | 3/1987 | European Pat. Off. . |
| 8902239 | 3/1989 | WIPO . |

OTHER PUBLICATIONS

Benz et al., Journal of Biological Chemistry 252(6):1908–1916. Mar. 25, 1977.
Arnold, Jr. et al. Clin. Chem. 35(8) 1588–1594, 1989.
Myers et al., "Detection of single base substitutions of total genomic DNA," *Nature* 313:495–498 (1985).
Myers et al., "Detection of Single Base Substitutions by Ribonuclease Cleavage at Mismatches in RNA:DNA Duplexes," *Science* 230:1242–1246 (1985).
Whitesides et al., "Magnetic separations in biotechnology," *Trends in Biotechnology* 1:144 (1983).
Chu et al., "Derivatization of unprotected polynucleotides," *Nucleic Acids Research* 11:513–6529 (1983).
Weeks et al., "Acridinium Esters as High–Specific–Activity Labels in Immunoassay," *Clin. Chem.* 29:1474–1469 (1983).
Hirschfeld, "Fluorescence Background Discrimination by Prebleaching," *J. of Histochemistry and Cytochemistry* 27:96–101 (1979).

*Primary Examiner*—W. Gary Jones
*Assistant Examiner*—Paul B. Tran
*Attorney, Agent, or Firm*—Lyon & Lyon LLP

[57] ABSTRACT

Improved homogenous diagnostic assay methods and labels for detecting an analyte in a medium when the analyte is a member of a specific binding pair. The methods and labels provide procedures for reducing background and increasing sensitivity. The binding partner of the analyte is labeled with a substance, the stability of which detectably changes whenever said analyte is bound as a member of the specific binding pair. In a closely related system, the analyte is labeled with a substance susceptible to differential degradation depending on whether or not the analyte is bound as a member of its specific binding pair. After incubation and selective degradation or chemical or biochemical alteration, the amount of analyte bound is detected by measuring either the stability change or the extent of degradation of the label. In a particular system, chemiluminescent acridinium ester labeled probes are used in a homogenous hybridization assay format for sensitively detecting the presence of complement any target polynucleotide sequences.

9 Claims, 5 Drawing Sheets

HOMOGENEOUS PROTECTION ASSAY

This application is a continuation of application Ser. No. 07/613,603, filed Nov. 8, 1990, now U.S. Pat. No. 5,283,174, which is a continuation of application Ser. No. 07/294,700, filed Dec. 12, 1988, now abandoned. This application is also a continuation-in-part of application Ser. No. 07/099,392, filed Sep. 21, 1987, now abandoned.

BACKGROUND

This invention is in the art of diagnostic procedures and techniques for detecting and quantitating minute amounts of organic compounds.

More particularly, this invention relates to homogeneous diagnostic assays in which there is a difference in the stability of the label in its bound, as opposed to its unbound forms. This invention relates to the construction of environments for diagnostic assay systems in which a label is differentially degraded in either its complexed or bound form as compared to its uncomplexed or unbound form.

BACKGROUND OF THE INVENTION

Diagnostic assays are a common analytical technique for detecting, locating or quantifying biological substances by employing labelled binding reagents. The presence of the labeled reagent can then be detected using a variety of known methods. This invention can be applied to all known diagnostic assay formats, including, without limitation, direct binding and competition assays and sequential saturation. One particular type of diagnostic assay is the nucleic acid hybridization assay. Hybridization assay systems are based on the fact that single stranded nucleic acids (DNA or RNA) will hybridize or recombine, under appropriate circumstances, with complementary single stranded nucleic acids. By labelling the complementary probe nucleic acid with a readily detectable label, it is possible to detect the presence of the target polynucleotide sequence of interest in a test sample containing single stranded nucleic acid sequences.

Assay systems may broadly be characterized as heterogeneous or homogeneous. The term "heterogeneous" as applied to assay systems means those specific binding assays which require a separation of the labelled from unlabeled substance to be detected. Homogeneous assays systems, on the other hand, do not involve any physical separation steps. Because homogeneous assay systems involve a minimum number of handling steps they are generally more convenient and easier to use than heterogeneous assay systems.

For example, a typical sandwich immunoassay may involve incubating an immobilized antibody with a test medium. Antigens, if in the medium, will bind to the antibody. After incubation, unbound antigen is removed in a separation step. After a second, or simultaneous incubation with a solution of labeled antibody, the bound antigen becomes "sandwiched" between the immobilized antibody and the labelled antibody. After a second separation step, the amount of labeled antibody can be determined as a measure of the antigen in the medium. This system is time consuming because it involves a series of incubation and separation steps.

A focus of effort of the prior art in diagnostic assays has been directed to developing homogenous assays and labels which can discriminate between minor differences in the amount of bound, as opposed to unbound substances of interest. One of the objects of the present invention is an assay system in which the label itself undergoes a detectable change, which may be, for example, in its ability to chemiluminesce, when it is in its bound, as opposed to when it is unbound. Another object of the present invention is an assay system in which the label is substantially degraded or destroyed in either its bound or unbound form, thereby providing a ready means for identifying and quantitating a reaction of interest.

It is an object of the present invention to disclose an improved method for sensitively detecting analytes using a homogeneous assay format. It is also an object of this invention to provide improved methods for increasing the sensitivity of assays which involve separation by combining the homogeneous method disclosed herein with other separation methods to reduce non-specific background. The principle of the invention disclosed here is based upon the differential stability of a label to chemical or biochemical reagents. Whenever certain labels are conjugated to binding partners, we have found that the stability of said labels are or may be altered when said binding partner is bound to a binding substance of said binding partner. It is also the object of this invention to disclose a method by which said differential label stability may be employed for the sensitive detection of an analyte employing a homogeneous diagnostic assay systems. Yet another object of the present invention is to disclose the use of chemiluminescent acridinium ester labeled DNA probes in said homogeneous diagnostic assays for sensitively detecting the presence of complementary target polynucleotide sequences.

DESCRIPTION OF THE PRIOR ART

There are a variety of homogeneous assays in the prior art which vary in complexity. In some systems, for example, the label is a catalyst which can participate in a chemical reaction in the presence of other components, for example, enzymes, coenzymes and cofactors. In other, albeit related systems, the label is a substrate for a chemical or biochemical reaction. In these systems, the generation of a specific readily detectable substance, for example, glucose, lactate or alcohol is used to monitor and measure the target reaction. In other assay systems, the label possesses unique physical properties which allow it to be directly detected. Examples of these types of labels include metals, hemoglobin and chlorophyl.

Still other homogenous assay systems are based on enzyme coupled specific binding reactions, wherein the analyte is a ligand for a specific binding reaction. When the analyte is present, it undergoes a specific binding reaction with a conjugate which is comprised of a specific binding partner and a labelling substance. Either concurrently or subsequently, other substituents are added which interact with the label. The activity of the label is different when the conjugate of which the label is a component, is in a complexed form verses an uncomplexed form. Such systems have typically used enzymes as the labelling reagent and substrates which produce a colorimetric, fluorimetric, or chemiluminescent end point. Examples of homogeneous enzyme immunoassays include U.S. Pat. Nos. 3,654,090, 3,817,837 and 4,190,496. Other examples of homogeneous assays involving the use of chromophores which make up fluorescer/quencher pairs may be found in U.S. Pat. Nos. 4,199,559, 4,174,384 and 4,318,707. In some systems, however, the label has been a substance other than an enzyme, for example, vitamins, NAD, FAD or biotin, which nevertheless can be coupled to a "monitoring" reaction. An example of this type is U.S. Pat. No. 4,383,031. In these systems, the monitoring reaction is based upon a structural change which modifies the activity of the label.

Other homogenous assay systems involve the technique of polarization fluorescence. Here, the analyte competes with a low molecular weight fluorescent conjugate for binding to a high molecular weight specific binding partner. Since the polarization of the fluorescence changes when the small molecule is displaced from the surface of the large molecule, it is possible to determine the amount of analyte in solution. An example of this type of assay system is U.S. Pat. No. 4,668,640.

Yet another type of homogenous assay system involves non-radiative energy transfer. In these systems, the absorption of light from one molecule to another when the two molecules come into close proximity is used as the monitoring reaction. Generally, these methods have been described in two ways. In one method, the first molecule is chemiluminescent and upon excitation a portion of the electromagnetic energy generated is transferred to a second "absorber" molecule which must be in close proximity. If the energy is absorbed by the second molecule and emitted at a different wavelength, a portion of the light will show a spectral shift proportional to the number of chemiluminescent molecules in close proximity to absorber molecules.

In another type of non-radiative energy assay systems, the first molecule is fluorescent and serves as an "absorber" of external light. In the presence of a second fluorescent molecule a portion of the energy is transferred and light is emitted at a different wavelength. The emitted light will show a spectral shift proportional to the number of "absorber" and "emitter" molecules in close proximity to each other.

A different type of double probe assay system is seen in U.S. Pat. No. 4,670,379. The first probe labeled with a catalyst; the second with an apoluminescer. Both probes target neighboring areas on the target nucleic acid sequence. Once both probes are hybridized together with the target, the substrate is added. The catalyst converts the substrate to a transformation radical which, in turn, converts the apoluminescer on the second probe to a luminescer. This occurs only if hybridization has taken place. Employing these principles, assays have been developed based upon two labelled substances simultaneously binding a common analyte.

A specific example of this type of energy transfer assay system is Elazar et al., European Patent Application No. 85105130.0, Publication No. 0159719 published Oct. 30, 1985, which discloses using two single stranded nucleic acid probes which are complementary to the same or opposite strands of the target genetic material. Each probe is labeled with a moiety capable of producing a signal only when the two labels are brought together. Unlike the invention herein described, Elazar et al. involves the formation and detection of double hybrid or multihybrids. Similarly, Heller et al., European Patent Application No. 82303699.1, Publication No. 0070685 dated Jan. 26, 1983 and related Morrison et al., European Patent Application No. 82303700.7, Publication No. 0070686 of the same date disclose homogenous assay systems using two luminescer probes. At least one of the light labels is of the absorber/emitter type so that when the two probes are hybridized to the target, energy transfer occurs between the two labels. This causes the absorber/emitter to re-emit at a different wavelength. The second emission detects hybridization. An antigen assay of this type is disclosed in Morrisson et al. supra.

Most biological substances can not be readily detected directly at any reasonable level of sensitivity and require a binding reaction of some type. As evident from the foregoing discussion, the prior art is based on the detection of minor attenuations between bound and unbound label. The prior art systems are not capable of significant discrimination between bound and unbound label. Such assays have been found useful for detecting analytes which are present only at high concentration, for example in the monitoring of various drugs in blood and urine.

There is a need in the area of clinical diagnostics for a direct detection homogenous assay which is based on the ability of two binding partners to modify the stability of the label, for example, resulting in selective removal or destruction of label in either the bound or unbound form. While Hirschfield, in *Florescence Background Discrimination by Prebleaching* J. Histochemistry and Cytochemistry, 27/1, 96–101 (1979) describes a somewhat related electrooptics technique involving photochemical bleaching which may destroy label molecules, or at least their fluorescence. The invention disclosed herein does not teach or suggest use of photochemical bleaching or any other technique for selective removal or destruction of a label in a diagnostic assay. The subject invention fulfills a present need in diagnostic assays as it is orders of magnitude more sensitive than the prior art. The range of sensitivity of the prior art is no better than the $10^{-13}$ mole range, while the present invention is sensitive in the $10^{-16}$ mole range.

SUMMARY OF THE INVENTION

Briefly, this invention comprises diagnostic assays and methods. The method may be used to detect an analyte in a medium, said analyte being part of a specific binding pair. When the medium suspected of containing the analyte is combined with a binding partner, a label substance attached to the binding partner is capable of undergoing a detectable change in stability or differential degradation whenever the analyte binds to the specific binding partner. In a specific embodiment, single stranded nucleic acid probes have been modified to contain labels at virtually any desired position or location on the probe. The probe labels are of different stability or susceptible to differential degradation depending on whether the target nucleic acid sequence is hybridized to the probe.

Notably, the present invention comprises assay systems whereby the label on the bound probe is stabilized relative to the unbound probe. This stabilization may be aided by intercalation. DNA intercalating compounds, including acridinium ester, are particularly, but not exclusively, suited for use in this inventive assay system. DNA intercalators are known to bind noncovalently to duplex DNA and are characteristically flat molecules which may insert between base pairs of the double helix of DNA. We have evidence which indicates that acridinium esters prefer to insert in regions rich in adenine and thymidine base pairs.

It should be understood that while the present invention hereinafter will be described with particular reference to acridinium ester labelled probes, the present invention contemplates the use of equivalent labels and assay formats which are susceptible to differential degradation or change in stability when the conjugate to which the label is a component is bound. As will be explained in more detail herein, other suitable label compounds include substances which are destabilized by the amines present on nucleic acids particularly those in the vicinity of the label on unhybridized probes. Moreover, label substances which can interact with hydrophobic environments, for example by intercalating between base pairs, also may be used.

This invention has application generally to any system involving the selective substantial degradation of the label when comparing its bound and unbound conjugated forms. Furthermore, because of the relative simplicity of the assay system, which does not involve any separation or washing steps, it is both faster and less expensive than conventional systems. The system can be more sensitive than conventional systems in those cases in which there are large differences in stability between the bound and unbound conjugated forms of the label because all of the residual or unbound label conjugate is destroyed and, therefore, not detected. Finally, the system is very versatile and can be used either alone, or in combination with other separation methods to achieve very low background noise. The present invention is useful in probe diagnostics, including infection and genetic and vital disease detection and cancer diagnosis.

BEST MODE AND DETAILED DESCRIPTION OF THE PREFERRED EMBODIMENTS

Figure 1:
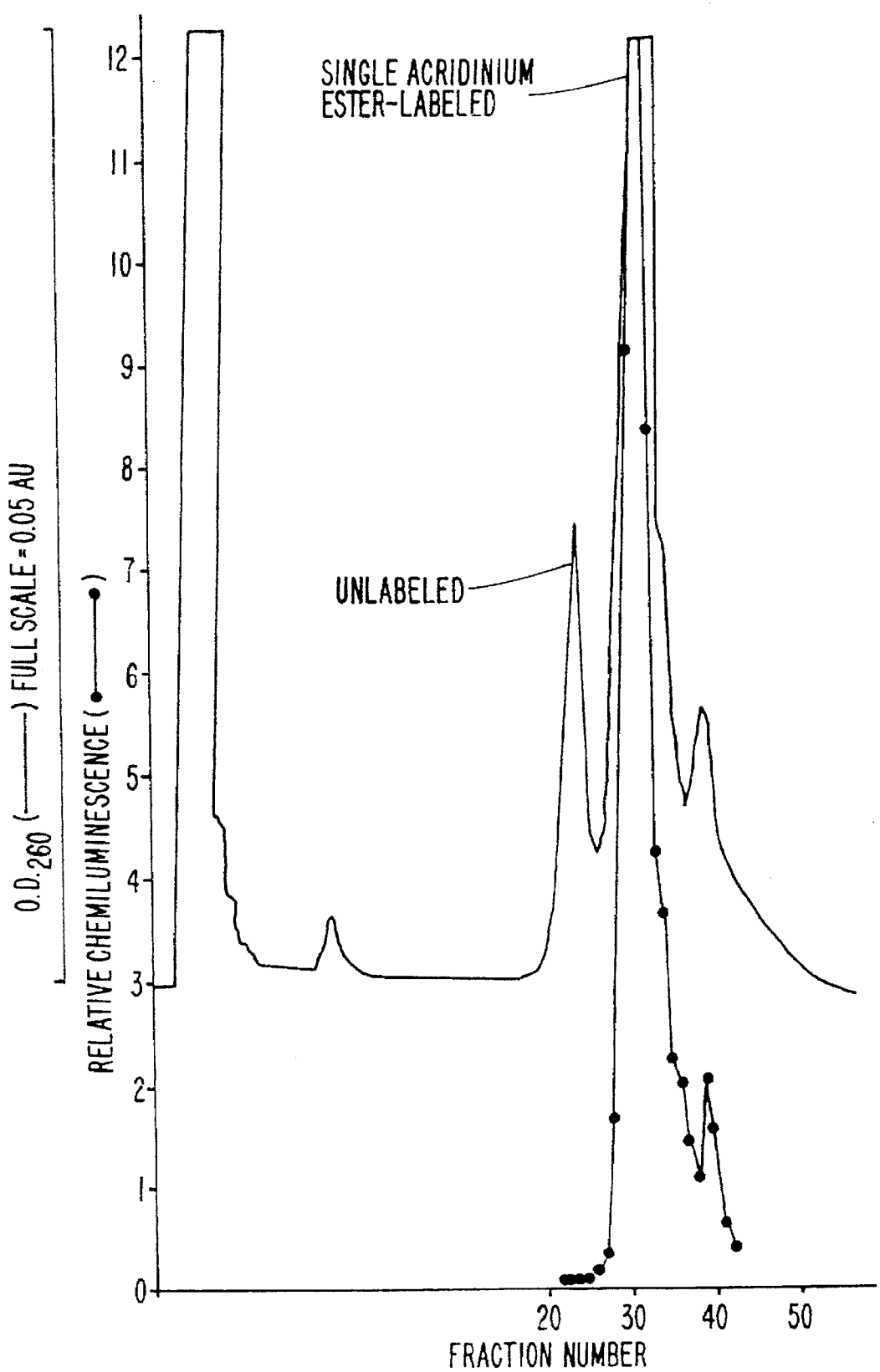
FIG. 1 is a graphical representation of HPLC purification of an acridinium ester-labeled probe.

The following definitions shall be used in this description:

1. acridunium ester: derivative of acridine possessing a quaternary nitrogen center and derivatized at the 9 position to yield a labile phenyl ester moiety, specifically, 4-(2-succinimidyloxycarbonyl ethyl) phenyl-10-methylacridiainium 9-carboxylate fluorosulfonate:

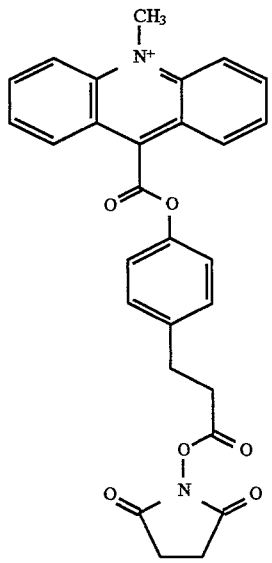

2. acridinium esters: moieties of the following general type:

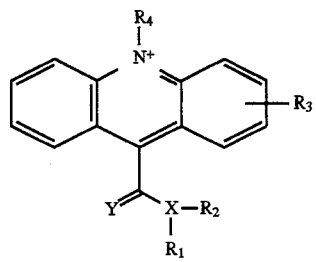

$R_1$=ALKYL, ALKENYL, ARYL, SUBSTITUTED ALKYL, SUBSTITUTED ALKENYL, SUBSTITUTED ARYL, ALKOXY, ARYLOXY, OR IS ABSENT WHEN X=HALOGEN.

$R_2$=H, ALKYL, ALKENYL, ARYL, SUBSTITUTED ALKYL, SUBSTITUTED ALKENYL, SUBSTITUTED ARYL, ALKOXY, ARYLOXY, IF AND ONLY IF X=N.

$R_3$=H, AMINO, HYDROXY, THIOL HALOGEN, NITRO, AMINO, AMIDO, ACETYL, ALKYL, ALKENYL, ARYL, SUBSTITUTED ACETYL SUBSTITUTED, ALKYL, SUBSTITUTED ALKENYL, SUBSTITUTED ARYL, ALKOXY, ARYLOXY.

$R_4$=ALKYL ALKENYL, ARYL, SUBSTITUTED ALKYL, SUBSTITUTED ALKENYL, SUBSTITUTED ARYL.

X=O, N, S, HALOGEN, SUBSTITUTED PHOSPHOROUS, SUBSTITUTED SULFUR, SUBSTITUTED BORON, OR SUBSTITUTED ARSENIC.

Y=O, S, OR NH.

$R_1$ AND/OR $R_2$ AND/OR $R_3$ AND/OR $R_4$ HAS A REACTIVE SITE WHICH ALLOWS CHEMICAL CONJUGATION.

3. analyte—any substance capable of undergoing a binding reaction with one or more specific binding partners, including, without limitation, antigens and antibodies thereto, haptens and antibodies thereto; hormones, drugs, metabolites, vitamins, coenzymes and their binding partners, including receptors; polynucleotides, oligonucleotides, and hybrids of polynucleotides or oligonucleotides and antibodies and binding substances thereto; polynucleotides or oligonucleotides and hybridizable polynucleotides or oligonucleotides thereto; metals and chelating agents thereto.

4. binding partner—any molecule or substance capable of undergoing a specific binding reaction with an analyte.

5. duplex: double stranded complex formed upon the annealing of two complementary, single stranded nucleic acid molecules.

6. hybridization: the formation of stable duplexes between 2 complementary single stranded DNA or RNA molecules or between a DNA and complementary RNA molecule. Duplex formation is specific for complementary base pairs, thereby reproducing the genetic code of the specific gene hybridized.

7. bound: condition in which a binding interaction has been formed between a molecule and its specific binding partner.

8. stable: resistant to chemical or biochemical degradation, rection, decomposition, displacement or modification.

9. stability: the resistance of a substance to chemical or biochemical degradation, reaction, decomposition, displacement or modification.

It is known that in solution acridinium esters exist in equilibrium with their corresponding bases. At high pH, base formation is favored; the quaternary nitrogen species reforms at low pH. It also is known that chemiluminescence reaction can be affected by adding base, specifically an aqueous solution of sodium hydroxide containing hydrogen peroxide. The chemiluminescence involves attack by hydroperoxide ions on the acridinium species, which results in the formation of electronically excited N-methylacridone. See generally, Weeks et al. *Acridinium Esters as High-Specific Activity Labels in Immunoassay,* Clin. Chem. 2918, 1474–1479 (1983). The reaction is diagrammed below.

so as to modify its ability to be detected, said degradation being possible under conditions which do not adversely effect the binding between the labeled binding partner and its binding substance and other binding partners and binding substances which may participate in the reaction. Preferred labels are ones which are affected in their ability to be detected after exposure to acids, bases, or selective oxidizing agents such as peroxidate, or enzymes.

Fourth, using chemical methods known in the art, attach the label to the binding substance at a site such that the

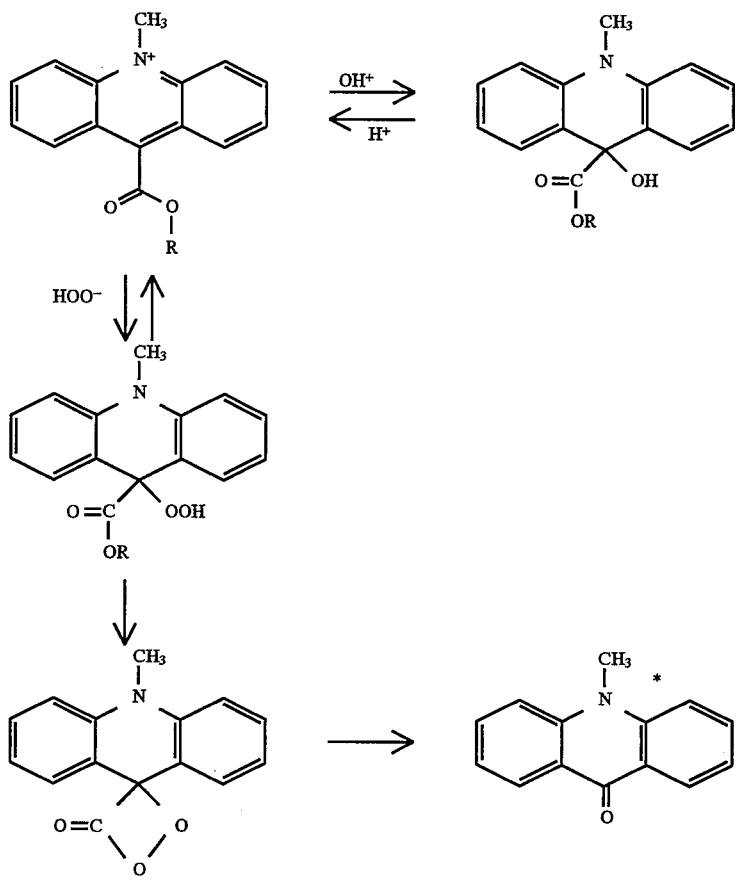

ACRIDINIUM ESTER REACTION SCHEME

The subject invention can be carried out as follows. First, select binding partners comprising a binding substance and one or more binding partners for the assay to be performed. These pairs may be antigens and antibodies thereto; haptens and antibodies thereto; hormones, drugs, metabolites, vitamins, coenzymes and their binding partners, including receptors; polynucleotides, oligonucleotides, and hybrids of polynucleotides or oligonucleotides and antibodies and binding substances thereto; polynucleotides or oligonucleotides, and hybridizable polynucleotides or oligonucleotides thereto; metals and chelating agents therefor.

Second, select the assay format to be used. These may be selected from formats comprising direct binding assays, competition assays, sequential saturation methods, and sandwich assays.

Third, select a label for the assay to be performed. This may be a label which can be directly or indirectly detected by colorimetric, fluorimetric, chemiluminescent, or bioluminescent means. The label should additionally have the property that it can be chemically or biochemically degraded label's sensitivity to chemical or biochemical degradation is modified upon interaction of the labeled binding partner with its specific binding substance(s). In some cases several different sites may be tested for label attachment and the site which gives the best differential degradation may be used.

Fifth, optimize the degradation conditions, be they chemical or biochemical, to give the best detection discrimination of the labeled binding partner in the presence and absence of its binding substance.

Finally, using the preselected assay format, test the ability of the assay system to detect quantitatively or qualitatively the analyte generally employing the steps of:
 a. Incubate
 b. Selectively degrade
 c. Detect
or
 a. Simultaneously incubate and selectively degrade
 b. Detect.

Employing this invention, oligonucleotide probes labelled with chemiluminescent acridinium esters are particularly useful for the detection of sequence specific polynucleotides through hybridization. Acridinium esters may be attached at a number of different sites on DNA probes and/or mixed nucleotide/non-nucleotide polymers as described in U.S. patent application Ser. No. (not yet assigned) filed Sep. 21, 1987 entitled "Non-Nucleotide Linking Reagents for Nucleotided Probes" by Arnold, et al. This includes the ability to label the nucleotide bases, the phosphate backbone, the 3' terminus, and the 5' terminus of oligonucleotides as well as the nonnucleotide monomeric units of mixed nucleotide/non-nucleotides polymers.

Such acridinium ester labeled probes can show significant differential chemical stability when the probes to which they are attached are free in solution as compared to when they are hybridized. This differential stability is dependent upon the position of the acridinium ester in the probe, the nucleotide residues in the vicinity of the acridinium ester label and the presence of other probe molecules which form stable hybrids with the target polynucleotide. A graphic representation is set forth below.

acridinium ester was further stabilized against degradation by intercalation into the hybrid duplex, particularly in regions of adenine/thymidine base pair density. We have found that a number of other insertion regions also give good differential hydrolysis, as explained in the following section.

There are several modes by which this invention may be applied to hybridization. These include without limitation:

1. Attaching the acridinium ester to the central region of the probe and near a region of adenine/thymidine base pairs. A preferred method is to attach an acridinium ester to a non-nucleotide monomeric unit as disclosed in U.S. patent application Ser. No. (not yet assigned), filed Sep. 21, 1987 entitled "Non-nucleotide Linking Reagents for Nucleotide Probes" by Arnold, et al. which is attached as an insert to nucleotide monomeric units which are complementary to immediately adjacent nucleotides of the target polynucleotide sequence. Such placement serves to restrict the amines of the nucleotide bases on both sides of the acridinium ester and to provide a site for intercalation.

2. Attaching the acridinium ester to either the 3' or 5' terminus of the probe and restricting the effects of nearby

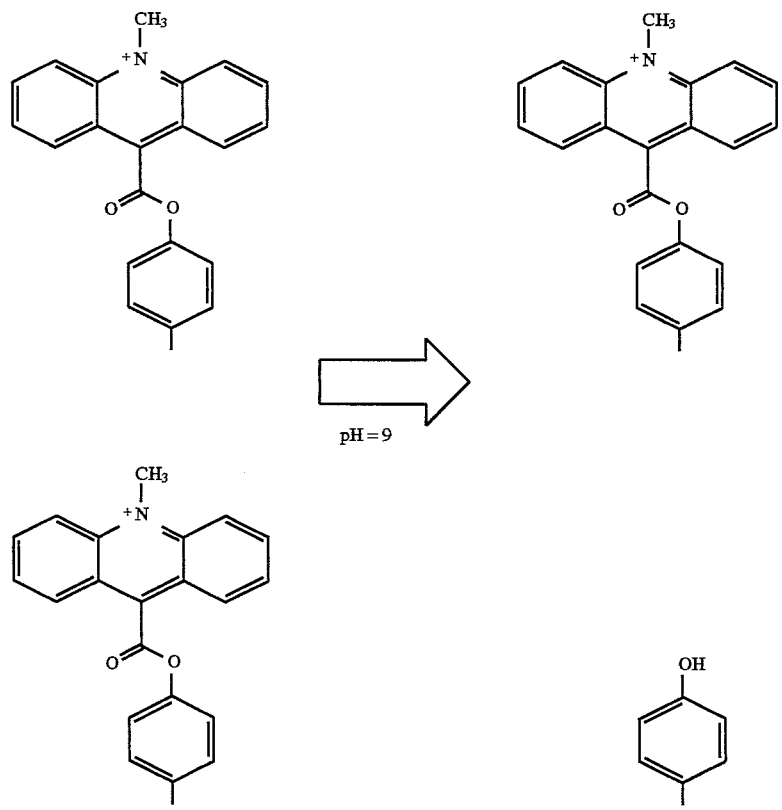

In the course of determining the factors which contribute to the differential stability of the acridinium ester on DNA probe molecules, we found that the free amines on the bases of unhybridized probes (both nucleotide and mixed nucleotide/non-nucleotide) destabilized the acridinium ester, especially in an alkaline environment. At the same time, if the acridinium ester is near the terminus of the probe, it can also be destabilized to alkali by amines contributed by target sequences once hybridizing occurs. When the probe hybridizes with a sequence specific polynucleotide (binding substance) the probe amines participate in base pairing with complementary nucleotides and are restricted in their ability to destabilize the acridinium ester, especially in an alkaline environment. At the same time, it was found that the amine contributed by the target polynucleotide with a second probe which hybridizes adjacent to the first. It may also be desirable if said second probe creates an A/T base pair rich region upon duplex formation. Even though this double probe or sandwich system is dependent upon the formation of two duplexes instead of only one, it may provide a method for sensitively detecting minor base pair changes which can be discriminated by very short probes i.e., probes of approximately 5–15 nucleotides in length.

3. Attaching the acridinium ester at or near the site of a mismatch with a polynucleotide sequence that is not the desired target polynucleotide. In this manner discrimination between polynucleotide sequences differing by only one nucleotide can be achieved, since the area of the duplex around a mismatch site is sufficiently destabilized to render the acridinium ester (if it is attached at or near this site) susceptible to degradation.

A preferred mode for the above three formats is to conduct the differential hydrolysis step at the same temperature as the hybridization step, typically at 50° to 70° C.

Another mode is to conduct a second differential hydrolysis step at room temperature. This allows pH's in the range of 10–11 to be used, yielding even larger differences in the rate of hydrolysis between hybridized and unhybridized acridinium Estes-labeled probe.

Under normal circumstances such short probes have the ability to discriminate single mismatches under appropriate hybridization conditions. As a practical matter, however, they are not used because they are not sufficiently specific for single polynucleotide sites. That is, the short probe may hybridize several specific sites contained within a multitude of complex DNA or RNA sequences present. With the added requirement, that two different probes must hybridize immediately to adjacent polynucleotide regions, such regions can be specifically targeted and identified. Thus, the benefits of short probe discrimination may be utilized while maintaining the specificity of the region spanned by both probes.

Experimental Methods and Materials

The following examples are offered by way of illustration and not by way of limitation. These examples are based on currently available data and the most likely explanations of the phenomenon. Other factors and methods may become evident with more research. Although the invention has been described in detail by way of illustration and examples using acridinium ester labels, certain changes and modifications may be practiced within the scope of the claims and other label systems also may be employed within the scope of the claims.

EXAMPLE 1

Construction of Acridinium Ester-Labeled Probes
A. Synthesis and Purification of Amine Linker-Arm Probes Deoxyoligonucleotide probes were synthesized to contain an amine liner-arm (i.e., one which terminates in a primary amine for labeling with acridinium ester) located either at the 5'-terminus, at some preselected location along the polyphosphate chain, in the internal portion of the probe or attached to one of the nucleotide bases.

(i)

To attach a 5'-amine linker-arm to a probe, the following compound was used:

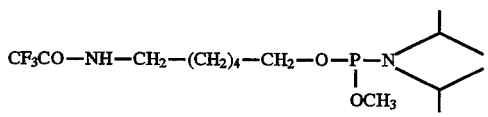
(1)

This compound will heretofore be referred to as terminal amine linker-arm reagent. This reagent was synthesized as follows: 6-amino hexanol was reacted with S-ethyltrifluorothioacetate in anhydrous ethylacetate. The reaction product was precipitated in petroleum ether, treated with a 10% pyridine in water mixture for 10 minutes to hydrolyze any 0-trifluoroacetyl which may have formed, and evaporated to dryness in the form of a gum. This compound was then phosphitylated according to standard protocols within the literature to yield the desired compound, namely, terminal amine linker-arm reagent (1).

Probes containing a 5'-amine linker-arm were synthesized as follows. Using an Applied Biosystems, Inc. Model 380A DNA synthesizer, probes of desired nucleotide sequence were produced using standard phosphoramidite chemistry, building the probes from the 3' end to the 5' end. After the desired sequence was completed, the amine linker-arm was automatically coupled to the 5'-hydroxyl group of the probe using the terminal amine linker-arm reagent in the same way another phosphoramidite nucleoside would have been coupled. Using standard protocols, the probe was then cleaved from the solid support, deprotected and purified by polyacrylamide gel electrophoresis followed by Sephadex G-25 chromatography.

The following probe was synthesized and purified using this procedure:

5'-NH$_2$-(CH$_2$)$_6$-GCTCGTTGCGGGACTTAACCCAACAT-3' where NH$_2$-(CH$_2$)$_6$ represents the amine linker-arm.

(ii)

To incorporate an amine linker-arm into the internal portion of a probe, internal amine linker-arm reagent, type 1 or type 2, was used as described in U.S. patent application Ser. No. 099,050 entitled "Non-Nucleotide Linking Reagents for Nucleotide Probes" filed Sep. 21, 1987 by Arnold, et al. Again, probes were synthesized using standard phosphoramidite chemistry and purified using polyacrylamide gel electrophoresis and Sephadex G25 chromatography.

The following probes were synthesized using this procedure:

1.) A 30 mer complementary to the 16S subunit of rRNA from *E. coli*, with an internal amine linker-arm, type 1, replacing an adenine residue at position 18 in the sequence:

|Replaced with an internal amine linker arm, type 1|
5'-CCA CTG CTG CCT CCC GT(A)GGA GTC TGG GCC-3'.

2.) A 33 mer complementary to the 16S subunit of rRNA from *Chlamydia trachomatis*, with an internal amine linker-arm, type 1, replacing an adenine residue at position 21 in the sequence,

|Replaced with an internal amine linker arm, type 1|
5'-CGT TAC TCG GAT GCC CAA AT(A)TCG CCA CAT TCG-3', or inserted between residues 21 and 22,

|An internal amine linker-arm, type 1 or type 2, inserted here|
5'-CGT TAC TCG GAT GCC CAA ATA▼TCG CCA CAT TCG-3'.

(iii)

Nucleotide bases containing amine linker-arm were incorporated into a probe as follows. Template and primer oligonucleotides with the following sequences were synthesized:

Template 3'—GCA ATG AGC CTA CGG GTT TAT AGC GG—5'

Primer 5'—CGT TAC TCG GAT GCC CAA AT—3'

(The primer and extended primer sequences are complementary to the 16S subunit of *C. trachomatis*.)

Primer extension using the Klenow fragment was performed as described in Maniatis (ref.), with the exception that the BSA was omitted from the 10× nick translation buffer, to incorporate the amine linker-arm modified base amino (12) dUTP (Calbiochem, Calif.). The sequence of the resulting oligomer is, therefore:

CGT TAC TCG GAT GCC CAA ATA (amino-12-U)CG CC.

Purification of the primer extended complex was achieved using a NENSORB-20 cartridge (DuPont) following the procedure recommended by the manufacturer. (The primer extension reaction was diluted by the addition of 900 µl of NENSORB reagent A prior to loading on the column. The purified oligomers were eluted with 50% methanol which was then removed in a speed-vac.)

B. Labeling of Amine Linker-Arm Probe with Acridinium Ester and Subsequent Purification A 25 mM stock solution of acridinium ester was prepared in distilled DMSO. The desired amount of probe (see a listing of the different probes labeled in section A above) was evaporated to dryness in a 1.5 ml conical polypropylene tube. The following cocktail was constructed by adding the following ingredients in the order listed:

3 µl $H_2O$
1 µl 1M HEPES (pH 8.0)
4 µl DMSO (distilled)
2 µl 25 mM acridinium ester in DMSO (distilled)

The mixture was vortexed, spun in a microcentrifuge for 2 seconds (to bring the contents to the bottom of the tube), and incubated at 37° C. for 20 minutes. The following components were then added to the reaction cocktail in the order listed:

3.0 µl 25 mM acridinium ester in DMSO (distilled)
1.5 µl $H_2O$
0.5 µl 1M HEPES (pH 8.0)

The cocktail again was vortexed, spun, and incubated an additional 20 minutes at 37° C. The unreacted label was quenched using a 5-fold excess of lysine by adding 5 µl of 0.125M lysine in 0.1M HEPES (pH 8.0), 50% DMSO, and incubated 5 minutes at room temperature.

The acridinium ester-labeled oligomer was then purified using the following method. To the 20 µl quenched reaction mixture 30 µl 3M NaOAc (pH 5.0), 245 µl $H_2O$ and 5 µl glycogen was added as a carrier (the glycogen was pre-treated to remove any nuclease activity). The sample was vortexed briefly and 640 µl of absolute EtOH added. The sample was vortexed briefly and incubated on ice 5–10 minutes, then centrifuged 5 minutes at 15,000 rpm in a microcentrifuge. The supernatant was carefully removed and the pellet was redissolved in 20 µl of 0.1M NaOAc (pH 5.0), 0.1% SDS. The samples were then purified by high performance liquid chromatography (HPLC) as described below.

(i)

The AE-labeled probes containing the 5' and internal amine linker-arms were purified as follows: the 20 µl redissolved pellet was injected onto a a Nucleogen-DEAE 60-7 ion-exchange HPLC column mounted in an IBM® 9533 HPLC system. All buffers were made with HPLC grade water, acetonitrile ($CH_3CN$) and sodium acetate (NaOAc) from Fisher Scientific, and reagent grade glacial acetic acid (HOAc) and LiCl. All buffers were filtered through 0.45 µm pore size Nylon-66 filters before use. The sample was eluted as described in FIG. 1 of the drawing (in this case the probe was the 5'-amine linker-arm containing 26 mer described in Section A above). Immediately after the run, 5 µl of 10% SDS was added to each tube followed by vortexing of each tube (this was done to ensure that the acridinium ester-labeled probe did not stick to the walls of the tube). A 0.5 µl aliquot was removed from fractions 21–42 and added to 200 µl water in a 12×75 mm tube (a separate pipet tip was used for each aliquot to avoid a carryover problem). The chemiluminescence of each aliquot was then determined in a Berthold Clinilumat using the following automatic injection and read sequence: injection of 200 µl of 0.25N $HNO_3$, 0.1% $H_2O_2$; a 1 second delay; a 200 µl injection of 1N NaOH; read chemiluminescent output for 10 seconds.

Fractions 29–33 were then EtOH precipitated as follows: Add to each fraction 5 µl glycogen, vortex, add 1 ml EtOH, vortex, incubate 5–10 minutes on ice, and centrifuge 5 minutes at 15,000 rpm in a microcentrifuge. Each supernatant was carefully removed, the pellet redissolved in 20 µl 0.1M NaOAc, pH 5, 0.1% SDS, and the fractions pooled.

In this manner, highly pure acridinium ester-labelled probes were obtained. The specific activity of such probes was typically 5–10×10$^7$ chemiluminescent light counts (Berthold Clinilumat) per picomole of oligomer.

(ii)

The AE-labeled probe containing the amine linker-arm modified base (amino-12-U) was purified generally as described above, with the following exceptions: A Vydac C4 reverse-phase column was used; buffer A was 0.1M tri-ethyammonium acetate (Applied Biosystems, Inc., Foster City, Calif.) and buffer B was $CH_3CN$; the labeled probe was eluted as a hybrid using a linear gradient for 10–15% solvent B in 25 minutes at a flow rate of 1 ml/min. The main chemiluminescent peak was then identified and worked up as described above.

The preceding discussion generally describes how to make and label probes with acridinium ester. In the specific example herein, probes were end and internal labeled, as well as labeled in a nucleotide base.

EXAMPLE 2

Stability at pH 6 of Hybridized Versus Unhybridized Probe Internally Labeled with Acridinium Ester An internally labeled 33 mer probe specific for *Chlamydia trachomatis* was prepared as previously described (adenine replacement, type 1 linker-arm). The probe was hybridized with its target rRNA (in this case *Chlamydia trachomatis*) according to the following procedure:

Hybridization mixture

2 µl AE-probe (0.5 pmol)
0.3 µl 4% (wt:vol) SDS
5.8 µl 1M PB, pH 5
4.4 µl *C. trachomatis* rRNA (2 µg), or 4.4 µl $H_2O$ for control.

The hybridization and control mixtures were incubated 40 minutes at 60° C., at which point each mixture was analyzed for percent hybridization using hydroxyapatite (HAP) as follows. A 0.1 µl aliquot of the hybrid or control mixture was added to 200 µl of 0.14M PB, pH 6.8, containing 2% HAP. Each resulting mixture was vortexed 5 seconds, incubated 5 minutes at 60° C., vortexed 20 seconds, then centrifuged 30 seconds in a microcentrifuge at 15,000 rpm. The supernatant was removed and saved, 200 µl of 0.14M PB, pH 6.8, was added to the HAP pellet, the mixture was vortexed 10 seconds, then centrifuged 30 seconds in a microcentrifuge at 15,000 rpm. The supernatant was removed and saved and the pellet was resuspended in 200 µl 0.14M PB, pH 6.8. A 50 µl aliquot of the resuspended HAP and each of the 2 supernatants were analyzed for chemiluminescence as described below, and the percent hybridized probe, i.e., the percent chemiluminescent signal associated with the HAP, was calculated.

The stability of hybridized probe versus unhybridized probe (i.e., control) was tested at pH 6 according to the following procedure:

Stability test mixture 12.3 µl hybrid or control from above

50 µl 1M PB, pH 6

2.5 µl 4% SDS

65 µl $H_2O$

These mixtures were vortexed briefly, and 5 µl aliquots were removed immediately ($t_o$) and analyzed for chemiluminescence as described below. The remainder of the mixtures were incubated at 60° C., and 5 µl aliquots were removed at various time points (see below) and analyzed immediately for chemiluminescence.

The chemiluminescence of each sample was measured by adding a sample aliquot to 200 µl $H_2O$ in a 12×75 mm tube and measuring chemiluminescence in a Clinilumat (automatic injection of 200 µl 0.25N $HNO_3$, 0.1% $H_2O_2$ followed after a 1 second delay, by auto-injection of 200 µl 2M potassium PB, pH 13.2, and reading of chemiluminescence for 10 seconds).

RESULTS

Figure 2:
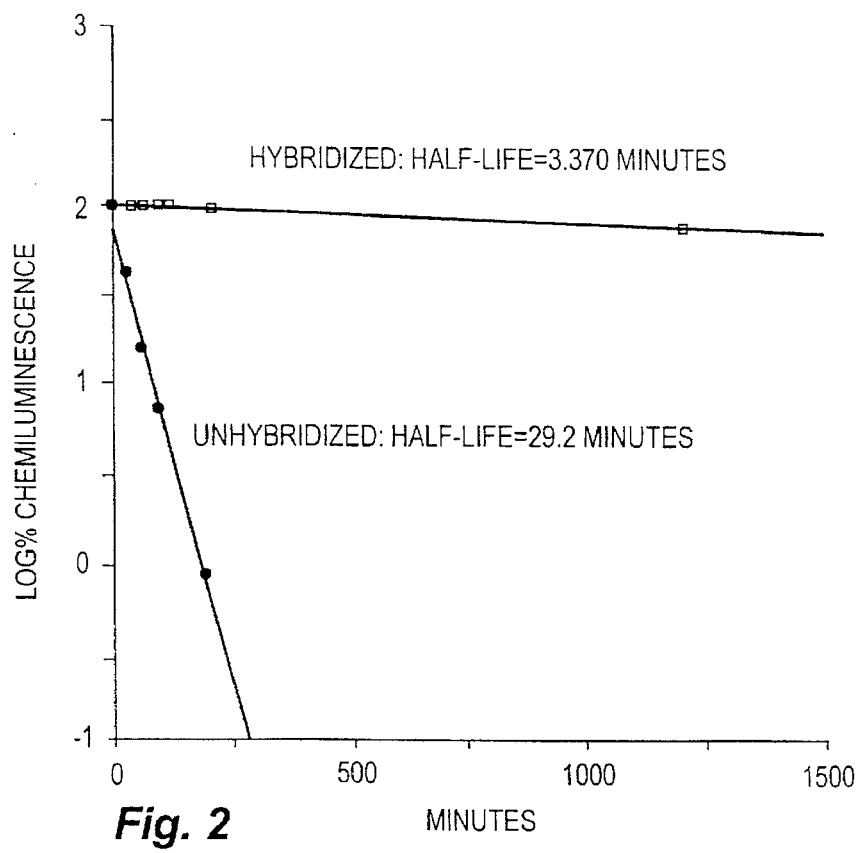
FIG. 2 is a graphical representation of the results set forth in Example 2.

1. Percent Hybridization (HAP analysis)
Hybrid—96%
Control—1.3% (non-specific binding)
2. Stability time course
See FIG. 2 of the drawing.

These results demonstrate that the hybridized probe is well protected against breakdown and subsequent loss of chemiluminescense (half-life for loss of chemiluminescence equal to 3370 minutes), whereas unhybridized probe is very susceptible to breakdown and loss of chemiluminescence (half-life is equal to 29.2 minutes; therefore, discrimination between hybridized and unhybridized is equal to 115-fold). These data demonstrate the ability of the homogeneous assay herein described to locate target DNA sequences by imparting differential stability between hybridized and unhybridized probe and measuring same.

EXAMPLE 3

Stability at pH 9 of Hybridized Versus Unhybridized Probe Internally Labeled with Acridinium Ester Internally labeled probe (all 3 internally labeled 33 mer probes described in Example 1 were tested) was hybridized with its target rRNA (in this case *Chlamydia trachomatis*) and analyzed for percent hybridization as described in Example 2.

The stability of hybridized versus unhybridized probe (i.e., control) was tested at pH 9 according to the following protocol:

Stability test mixture

5 µl hybrid or control from above

45 µl 0.2M sodium borate, pH 9

The mixtures were then incubated, sampled and analyzed for chemiluminescence as described in Example 2.

RESULTS

1. Percent Hybridization (HAP analysis)
  a. Adenine replacement, type 1 linker-arm
    Hybrid—95%
    Control—0.5% (non-specific binding)
  b. Insertion, type 1 linker-arm
    Hybrid—98%
    Control—0.3%
  C. Insertion, type 2 linker-arm
    Hybrid—98%
    Control—0.2%

2. Stability time course

Figure 3:
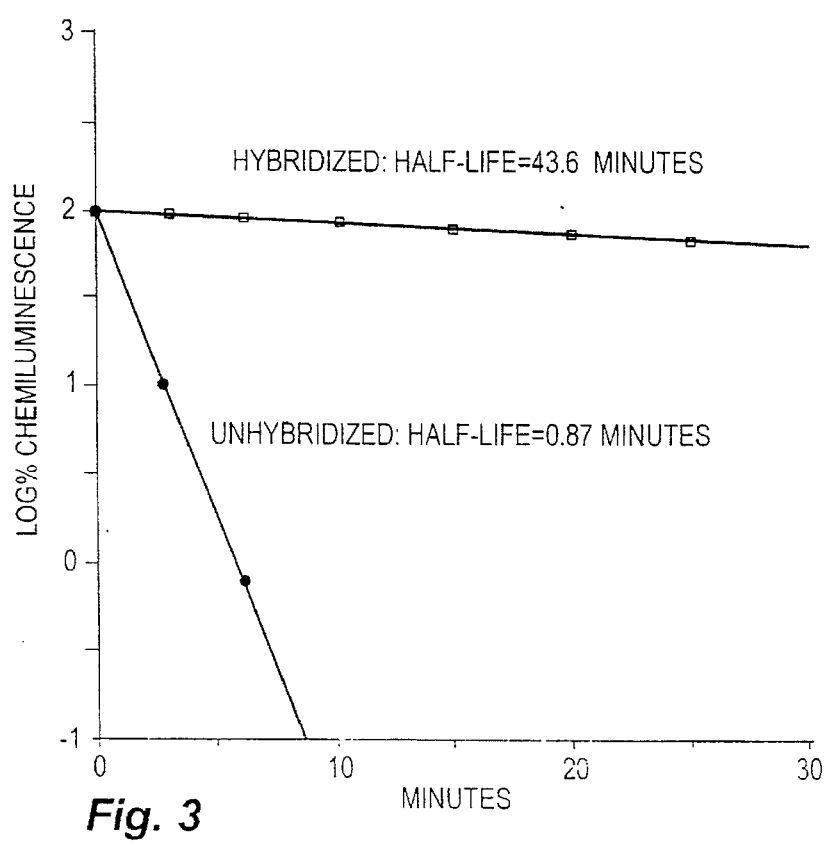
FIGS. 3–5 are graphical representations of the results set forth in Example 3.
Figure 4:
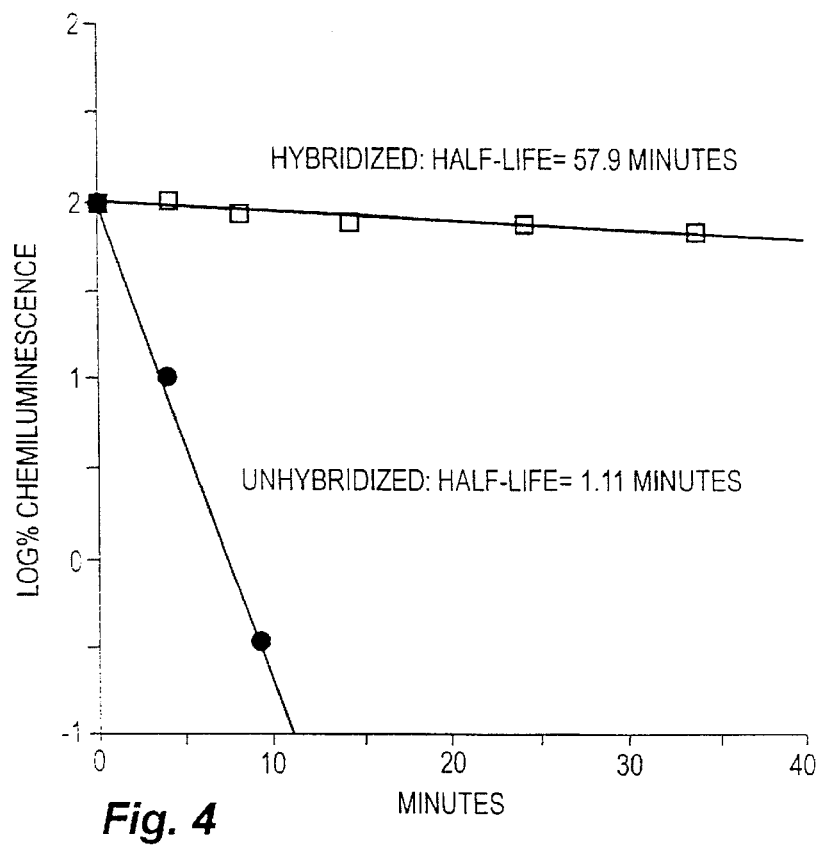
Figure 5:
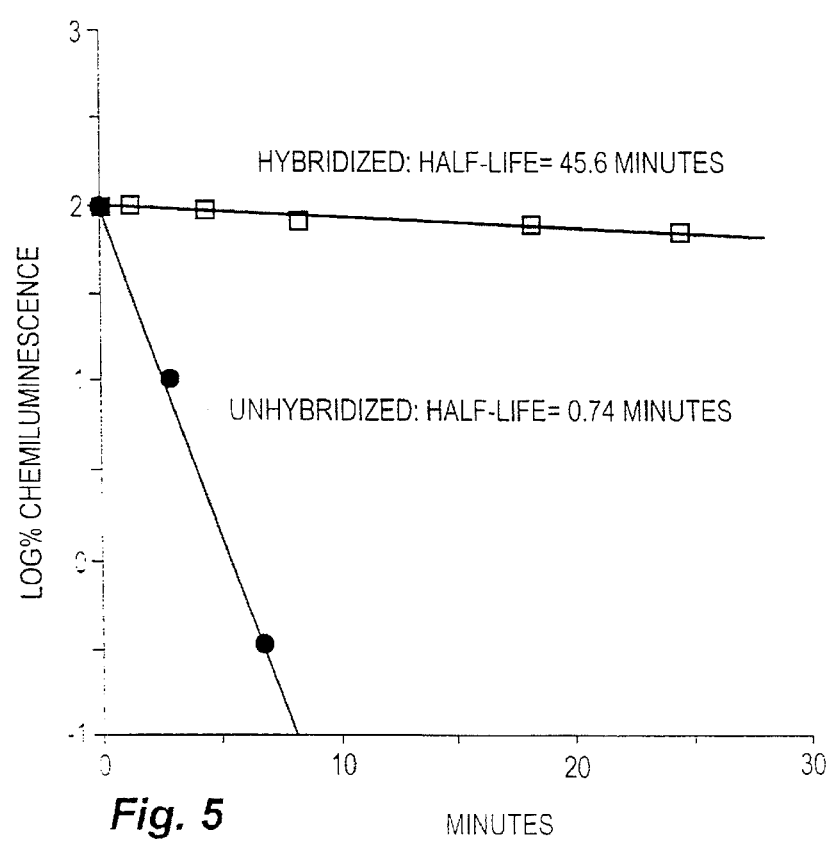

See FIGS. 3–5 of the drawing. FIG. 3 is a graph for adenine replacement, type 1 linker-arm; FIG. 4 is a graph of insertion, type 1 linker-arm; FIG. 5 is a graph of insertion, type 2 linker-arm.

As in Example 2, hybridized probe is protected from degradation whereas unhybridized probe is not. This is true for all three types of internally labeled probes. In this example, sodium borate at elevated pH is shown to accelerate this process (as compared with example 2) while still retaining the differential degradation characteristics between hybridized and unhybridized probe.

EXAMPLE 4

Stability at pH 6 of Probe End Labeled with Acridinium Ester as Hybrid with Adjacent Probe Versus Non-Hybrid This example involves use of a probe of sequence 5'-CCG GAC CGC TGG CAA CAA AGG ATA AGG GTT GC-3' (prepared using standard phosphoramidite chemistry) which hybridizes to *E. coli* rRNA immediately adjacent to the 5' end of the AE-labeled probe used in this example (see below), thereby leading to the "capping off" of all the amines in the target rRNA in the vicinity of the acridinium ester label.

Probe end-labeled with acridinium ester (preparation described in Example 1) (hereinafter referred to as AE-probe) and the adjacent probe described above were hybridized according to the following procedure:

| Hybridization mixture | Control mixture |
| --- | --- |
| 1 µl AE-probe (.25 pmol) | 1 µl AE-probe (.25 pmol) |
| 2 µl *E. coli* rRNA (2 ug) | 5.4 µl $H_2O$ |
| 4.3 µl adjacent probe (12 pmol) | 5.8 µl 1M PB, pH 5 |
| 0.3 µl 4% SDS | 0.3 µl 4% SDS |
| 7.5 µl 1M PB, pH 5 | |

The hybridization and control mixtures were incubated 40 minutes at 60° C., and then analyzed for percent hybridization using hydroxyapatite as described in Example 2.

The stability of the hybridized probe with adjacent probe versus unhybridized probe (i.e., control) was tested at pH 6 exactly as described in Example 2.

RESULTS

Figure 6:
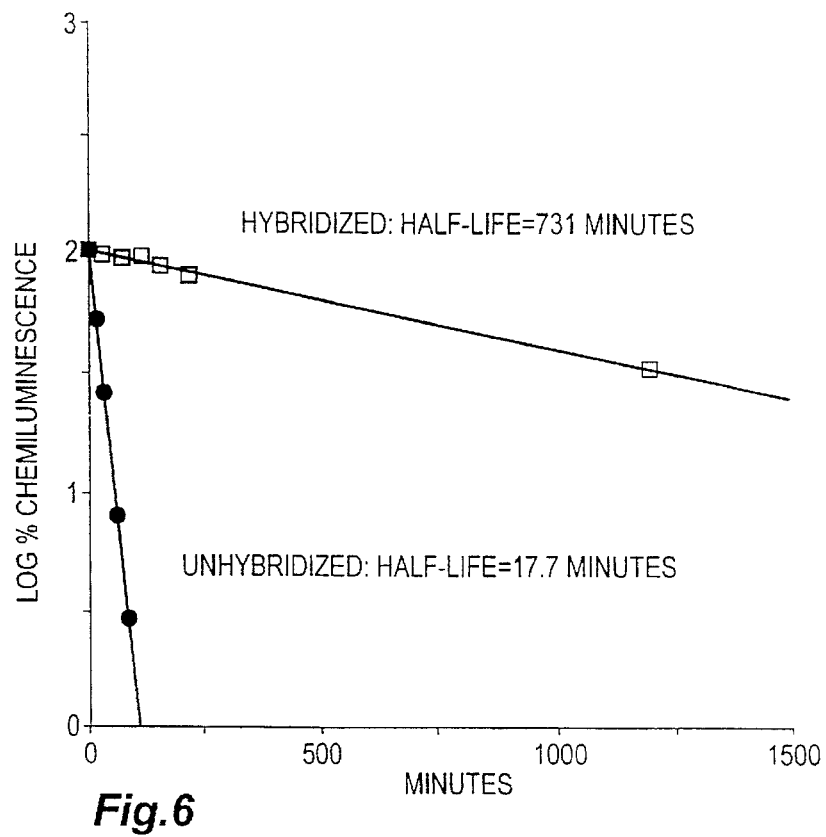
FIG. 6 is a graphical representation of the results set forth in Example 4.

1. Percent hybridization (HAP analysis)
Hybrid—93.5%
Control—2.7% (non-specific binding)
2. Stability time course.
See FIG. 6 of the drawing.

As in Example 2, hybridized AE-probe, in this case with an adjacent probe also hybridized, was protected from degradation whereas unhybridized probe was not. The protection was as good as in Example 2, because it is dependent on two hybridizations instead of one.

EXAMPLE 5

Stability at pH 9 of Probe End Labeled with Acridinium Ester as Hybrid with "Adjacent" Probe Versus Non-Hybrid Hybridization was carried out exactly as described in Example 4. Stability of hybridized probe with adjacent probe versus unhybridized probe (i.e., control) was tested at pH 9 exactly as described in Example 2, except the composition of the stability test mixture, which was as follows:

5 µl hybrid or control

50 µl 0.2M sodium borate, pH 9.0

Figure 7:
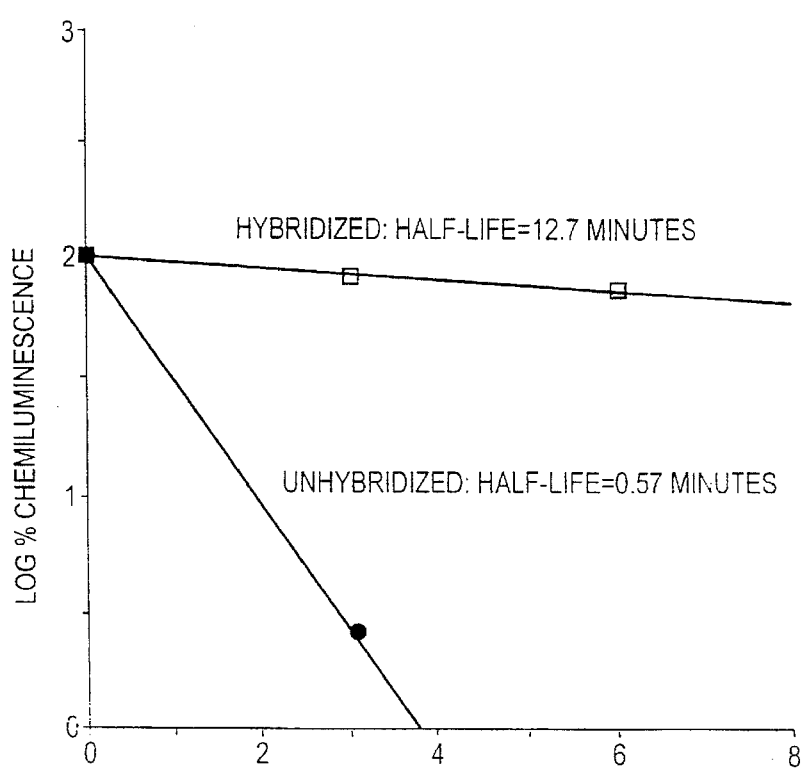
FIG. 7 is a graphical representation of the results set forth in Example 5.

Hybridized AE-probe with an adjacent probe (also hybridized) again was protected from degradation whereas unhybridized probe was not. As in Example 3, sodium borate at elevated pH accelerated the process while still retaining the differential degradation characteristics between hybridized and unhybridized probe. See FIG. 7 for a graphical representation of these results.

EXAMPLE 6

Stability at pH 6 of Probe End Labeled with Acridinium Ester as Hybrid Versus Non-Hybrid Probe was hybridized to its target rRNA (in this case *E. coli*) according to the following procedure:

| Hybridization mixture | Control mixture |
|---|---|
| 1 μl AE-probe (.25 pmol) | 1 μl AE-probe (.25 pmol) |
| 2 μl *E. coli* rRNA (2 ug) | 5.4 μl H$_2$O |
| 5.8 μl 1M PB, ph 5 | 5.8 μl 1M PB, pH 5 |
| 0.3 μl 4% SDS | 0.3 μl 4% SDS |
| 3.4 μl H$_2$O | |

The hybridization and control mixtures were incubated 40 minutes at 60° C., and then analyzed for percent hybridzation using hydroxyapatite as described in Example 2.

The stability of the hybridized probe versus unhybridized probe (i.e., control) was tested at pH 6 exactly as described in Example 2.

RESULTS

1. Percent hybridization

Hybrid—94%

Control—2.7% (non-specific binding)

2. Stability time course

Figure 8:
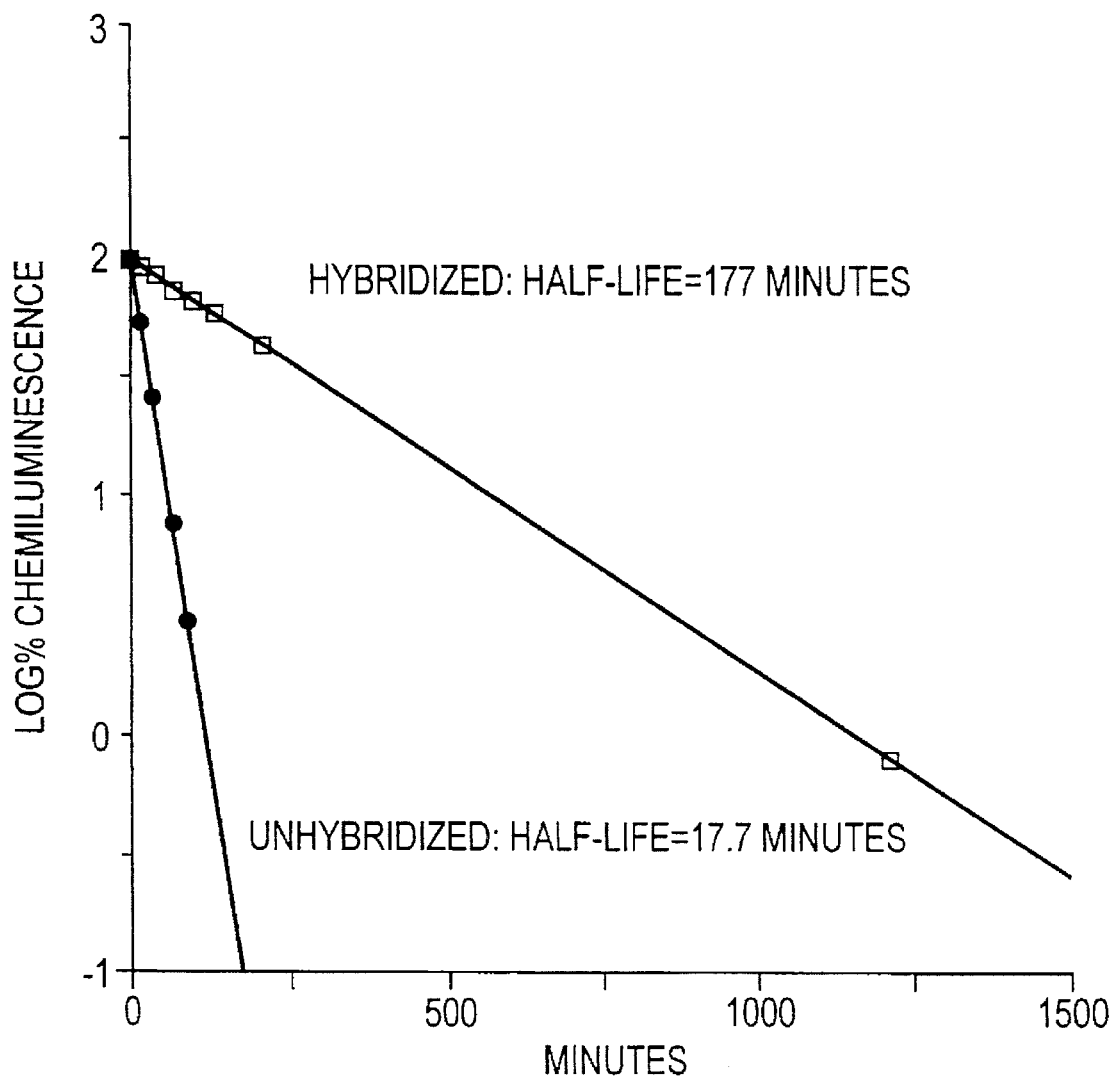
FIG. 8 is a graphical representation of the results set forth in Example 6.

See FIG. 8 of the drawing.

Unhybridized probe again was preferentially degraded as compared to hybridized probe, although the differential in degradation is not as great as in previous examples. This is because only a portion of the amines were "capped off" in the vicinity of the acridinium ester label. Indeed, this additionally demonstrates the ability to discriminate between hybridized end-labeled probe in the presence and absence of hybridized adjacent probe.

EXAMPLE 7

Stability at pH 7.6 of Hybridized Versus Unhybridized Probe Labeled on a Nucleotide Base with Acridinium Ester The probe labeled on a nucleotide base (amino-12-U) with acridinium ester described in Example 1, was hybridized with its target rRNA (in this case *C. trachomatis*) according to the following procedure:

Hybridization Mixture 0.1M lithium succinate, pH 5.4

10% lithium lauryl sulfate

2 μg 1.3 pmol AE-probe

Total volume—30 μl

The hybridization and control mixtures were incubated 5 minutes at 80° C., followed by 60 minutes at 60° C. The resulting solutions were each diluted to 300 μl with 0.1M lithium succinate, pH 5.4, 10% lithium lauryl sulfate, and analyzed for percent hybridization using hydroxyapatite as described in Example 2.

The stability of hybridized versus unhybridized probe (i.e., control) was tested at pH 7.6 with several identically prepared samples according to the following protocol:

Stability test mixture

15 μl hybrid or control from above

100 μl 0.2% sodium tetraborate, pH 7.6, 5% Triton X-100.

These mixtures were then incubated at 60° C., and samples were removed at various time points and chemiluminescence was determined using a Gen-Probe Leader™ I Luminometer employing the automatic injection of 200 μl of 0.1M H$_2$O$_2$, a 1-second delay, the automatic injection of 200 μl of 1N NaOH, and reading of chemiluminescence for 5 seconds. From these data the rates of hydrolysis were determined by regression analysis.

Results:

1. Percent Hybridization (HAP Analysis)

Hybrid—53.8%

Control—0.5%

2. Stability

Half-life of ester hydrolysis (min) Ratio of half-lives

| Hybrid | Control | (Hybrid/Control) |
|---|---|---|
| 13.6 | 1.3 | 10.5 |

As in preceding examples, these data demonstrate that hybridized probe is protected against degradation whereas unhybridized probe is not, in this case with the label attached to a base of the probe. This demonstrates the principle that multiple sites for AE attachment are acceptable for use in the homogeneous protection assay described herein.

EXAMPLE 8

Stability at pH 7.6 of Hybridized Versus Unhybridized Probes Internally Labeled with Acridinium Ester at a Variety of Sequence Dimer Sites Using Both rNA and DNA Targets Probes containing the internal linker-arm, type "X", inserted at a variety of sequence dimer sites (see below) were synthesized, labeled with AE, and purified as described in Example 1. The sequence and linker-arm locations of these probes are as follows:

| Probe No. | Sequence; linker-arm location (#) |
|---|---|
| 1 | 5' -GCT CGC TGC GGA CTT#AAA CCA ACA T-3' |
| 2 | 5' -AGG TCG GTC T#TT CTC TCC TTT CGT CTA CG-3' |
| 3 | 5' -CAA TCG TCG AAA CCA TT#G CTC CGT TCG A-3' |
| 4 | 5' -CCG CTA#CCC GGT ACG TT- 3' |
| 5 | 5' TTG CCC ACA CCG A#CG GCG- 3' |
| 6 | 5' -TTG CCC ACA CCG C#CG GCG- 3' |

These probes were hybridized as described in Example 7 with the exception that the 80° C. incubation step was omitted, and the amounts and types of target nucleic acids used were as follows:

| Probe # | Target Nucleic Acid |
|---|---|
| 1 | 1 μg of *E. coli* rRNA |
| 2 & 3 | 1 μg of *Q. trachomatis* rRNA |
| 4 | 1 μg of *N. gondrrhoeae* rRNA |
| 5 & 6 | 1.2 pmol of the exact synthetic DNA complement |

The stability of hybridized versus unhybridized probe was tested at pH 7.6 as described in Example 7.

RESULTS

| | Stability Ratio of half-lives | | |
|---|---|---|---|
| | Half-life of ester hydrolysis (min) | | |
| Probe # | Hybrid | Control | Hybrid/Control |
| 1 | 41.2 | 0.94 | 43.7 |
| 2 | 24.2 | 0.71 | 34.5 |
| 3 | 40.7 | 0.96 | 42.4 |
| 4 | 15.7 | 1.2 | 13.1 |
| 5 | 11.1 | 1.0 | 11.1 |
| 6 | 22.6 | 0.74 | 30.5 |

These data demonstrate that the linker-arm (and therefore the AE) can be inserted at a wide variety of sequence dimer sites and still be substantially protected against ester hydrolysis in the hybridized form. Furthermore this example demonstrates that DNA targets provide good protection of hybridized AE-probes when employed with these homogeneous assay formats. This example also demonstrates that the long (9 atom) linker-arm used here yields differential hydrolysis ratios essentially equivalent to the other linker-arms cited earlier in this patent establishing that a wide variety of linker-arm lengths can be used in the HPA format described herein.

EXAMPLE 9

Stability at pH 7.6 of Internally Labeled AE-Probe Hybridized with Perfectly Matched Target Versus Target with a Single Mismatch A 24 mer probe complementary to the 16S subunit of rRNA from *E. coli*, with an internal amine linker-arm, type "X", inserted between residues 6 and 7 was synthesized. The probe was then labeled with acridinium ester and purified and described in Example 1. The sequence is as follows (#=linker-arm position):

5'-CAA GCT# TGC CAG TAT CAG ATG CAG-3'

This probe has a single, T-G mismatch at position 6 (numbered from the 5' end of the probe strand) with the 16S subunit of *C. diversius*.

The probe was hybridized with its target rRNA (in this case either *E. coli* or *C. diversius*) according to the procedure described in Example 8. The stability of the resulting hybridized probes, as well as a sample of unhybridized probe was tested at pH=7.6 as described in Example 7.

Stability

Ratio of half-lives

| | Stability Ratio of half-lives | | |
|---|---|---|---|
| | Half-life of ester hydrolysis (min) | | |
| Target | Hybrid | Control | Hybrid/Control |
| *E. coli* | 18.6 | 0.8 | 23.3 |
| *C. diversius* | 1.1* | 0.8 | 1.4 |

*The low half-life of ester hydrolysis was not due to low hybridization extent, as HAP analysis (as described in Example 2) revealed 73% hybridization.

These data show that in the case of the hybrid with the perfectly matched target the AE-probe is protected from ester hydrolysis (as described in previous examples), whereas in the hybrid with the target containing a single base mismatch the AE-probe is poorly protected. This gives rise to a 17-fold difference in hydrolysis rate of the AE-probe between the perfect target and a single site mismatch target. Therefore, the method described herein is readily able to discriminate between nucleic acid targets containing single base differences.

EXAMPLE 10

Stability at Room Temperature Under Various conditions of Hybridized Versus Unhybridized Probe Internally Labeled with Acridinium Ester Internally labeled probe (insertion, type 1; see Example 1) was hybridized with 1 μg of *C. trachomatis* rRNA as described in Example 8. The stability of the hybridized versus unhybridized probe was measured at room temperature under a variety of reagent and pH conditions (see "Results") according to the procedure described in Example 7.

RESULTS

| BUFFER | pH | TEMP | HYBRID | CONTROL | RATIO |
|---|---|---|---|---|---|
| 0.2M borate 5% Triton | 7.6 | 60° C. | 34.13 | 0.89 | 38.08 |
| 0.2M borate 5% Triton | 7.6 | 40° C. | 272 | 7.5 | 36.26 |
| 0.2M borate 5% Triton | 7.6 | Room Temp. | 2307.7 | 61 | 37.82 |
| 0.2M borate 5% Triton | 9.0 | Room Temp. | 468.75 | 7.7 | 60.87 |
| 0.2M borate 5% Triton | 10.0 | Room Temp. | 98.36 | 1.3 | 73.78 |
| 0.2M borate 5% Triton | 11.0 | Room Temp. | 5.6 | 0.79 | 7.08 |
| 50 mM phytic acid, 0.05% SDS | 10.0 | Room Temp. | 145.48 (fast)* 398.55 (slow)* | 2.18 | 66.73 (fast)* |
| 50 mM phytic acid, 0.05% SDS | 11.0 | Room | 175.44 | 1.31 | 133.92 |

*In the phytic acid system, the hydrolysis kinetics were biphasic. "Fast" refers to the early, fast phase of hydrolysis, and "slow" refers to the later, slow phase of hydrolysis.

These date demonstrate that there are a wide variety of conditions under which the homogeneous protection assay described herein will function, making it adaptable to a wide range of assay conditions. Furthermore, systems other than borate are acceptable, for example, the phytic acid system at room temperature where very high half-life ratios are achieved.

EXAMPLE 11

Detection of a Dilution Series of Chlamydia rRNA in Buffer using Probe Internally Labeled with Acridinium Ester Internally labeled probe (as in Example 2) was hybridized to decreasing amounts of its target rRNA (in this case *Chlamydia trachomatis*) according to the following procedure:

Hybridization mixture 0.5 µl probe (12.5 fmol)

1 µl RNA ($10^{-2}$, $10^{-3}$, $10^{-4}$ or $10^{-5}$ µg)

2 µl 20% SDS 1.7 µl $H_2O$ 4.8 µl 1M PB, pH 6.8

The control mixture was the same as hybridization mixture except that it contained water instead of rRNA, and the reagent blank mixture was the same as the control mixture except that it contained water instead of probe. The mixtures were incubated 20 minutes at 60° C.

After hybridization, 90 µl of 0.2M borate, pH 9, was added to each sample, followed by incubation at 60° C. for 14 minutes. Each sample was then read for chemiluminescence as described in Example 2, except that injection 1 was 0.1% $H_2O_2$ only, injection 2 was pH 13.8 instead of 13.2, and the read time was 7 seconds instead of 10 seconds.

RESULTS

| Reagent blank - 116 rlu | | |
|---|---|---|
| Control - 124 rlu | | |
| | | Minus control |
| $10^{-5}$ µg rRNA - 126 rlu | | 2 rlu |
| $10^{-4}$ µg rRNA - 210 rlu | | 86 rlu |
| $10^{-3}$ µg rRNA - 1100 rlu | | 976 rlu |
| $10^{-2}$ µg rRNA - 7809 rlu | | 7685 rlu |

Reagent blank and control represent average of triplicates; all others represent average of duplicates.

These results demonstrate that the invention described herein was able to detect a linear dilution series of target rRNA to a limit of sensitivity of about $10^{-4}$ µg in a pure buffer system.

EXAMPLE 12

Detection of a Dilution Series of Chlamydia rRNA in Clinical Media using Probe Internally Labeled with Acridinium Ester Internally labeled probe (as in Example 2) was hybridized in clinical specimen (throat swab) to decreasing amounts of its target rRNA (in this case *Chlamydia trachomatis*) according to the following procedure:

Hybridization mixture

50 µl throat swab

60 µl 4.8M PB, pH 4.7

2 µl rRNA ($3\times10^{-4}$, $3\times10^{-3}$, $3\times10^{-2}$ or $3\times10^{-1}$ µg)

2 µl probe (1 pmol)

Control mixture was the same as hybridization mixture except that it contained water instead of rRNA, and the reagent blank mixture was the same as control mixture except that it contained water instead of probe. The mixtures were incubated 60 minutes at 60° C.

After hybridization, one third of each mixture (20 µl) was added to 50 µl 0.2M borate, final pH=9 (after addition of hybridization mixtures), followed by incubation at 60° C. for 40 minutes. Each sample was then read for chemiluminescence as described in Example 11.

RESULTS

| Reagent blank | 163 rlu | |
|---|---|---|
| Control | 6560 rlu | |
| | Minus control | |
| $10^{-3}$ µg rRNA | 8535 rlu | 1975 |
| $10^{-2}$ µg rRNA | 27306 rlu | 20746 |
| $10^{-1}$ µg rRNA | 258194 rlu | 251634 |

Data represent average of duplicate values.

These data demonstrate that the invention described herein was able to detect a linear dilution series of target rRNA to a limit of sensitivity of about $10^{-3}$ µg in a system containing clinical media.

EXAMPLE 13

Detection of a Dilution Series of Bacterial rRNA in Urine using Probe Internally Labeled with Acridinium Ester An internally labeled 30 mer probe specific for *E. coli* was prepared as previously described (adenine replacement, type 1 linker-arm). The probe was hybridized in urine to decreasing amounts of its target rRNA (in this case *E. coli*) according to the following procedure:

Hybridization mixture 79.6 µl urine 0.4 µl 0.25M EDTA, 0.25M EGTA

10 µl 4.8M PB, pH 6.8

5 µl 20% SDS

5 µl probe (0.125 pmol)

1 µl RNA ($10^{-3}$, $10^{-2}$, or $10^{-1}$ µg)

Control mixture was the same as hybridization mixture except that it contained water instead of rRNA, and the reagent blank mixture was the same as control mixture except that it contained water instead of probe. The mixtures were incubated 30 minutes at 60° C.

After hybridization, 300 µl 0.2M borate, pH 9, was added to each sample, followed by incubation at 60° C. for 16 minutes. Each sample was then read for chemiluminescence as described in Example 11.

RESULTS

| Reagent blank | 6845 rlu | |
|---|---|---|
| Control | 9250 rlu | |
| | Minus Control | |
| $10^{-3}$ µg rRNA | 9358 rlu | 8 rlu |
| $10^{-2}$ µg rRNA | 14055 rlu | 4805 rlu |
| $10^{-1}$ µg rRNA | 61800 rlu | 52550 rlu |

Results represent the average of duplicate values.

These data demonstrate that the invention described herein was able to detect a linear dilution series of target rRNA to a limit of sensitivity of approximately $5\times10^{-3}$ µg RNA in a system containing urine.

EXAMPLE 14

Selective Degradation used in Combination with a Separation Step for Detection of a Dilution Series of Chlamydia rRNA in Clinical Media using Probe Internally Labeled with Acridinium Ester Internally labeled probe (as in Example 2) was hybridized in clinical specimen (throat swab) as described in Example 8, including control and blank mixtures. After hybridization, one-third of each mixture was removed and subjected to selective degradation exactly as described in Example 8, while one-third was simply removed and allowed to stand at room temperature (i.e., no selective degradation). Both sets of samples, namely, with and without selective degradation, were then subjected to separation of hybridized from unhybridized probe using HAP as described in Example 2 with the following exceptions;

a. 1 ml of HAP solution was used (instead of 200 µl),
b. 1 ml of wash solution was used (instead of 200 µl),
c. 3 washes were performed (instead of 1),
d. The final HAP pellets were resuspended in 100 µl of wash solution, the entirety of which was measured for chemiluminescence (as described in Example 2).

RESULTS

| | SELECTIVE DEGRADATION | | |
|---|---|---|---|
| Minus | S:B | Plus | S:B |
| Control (no rRNA) | 18 | — | 4.7 | — |
| $10^{-3}$ µg rRNA | 27 | 1.5 | 10 | 2.1 |
| $10^{-2}$ µg rRNA | 117 | 6.5 | 70 | 15 |
| $10^{-1}$ µg rRNA | 933 | 52 | 591 | 126 |
| 0.33 µg rRNA | 2756 | 153 | 1755 | 373 |

Results represent the average of duplicative values with reagent blank already substracted. S:B=signal to background ratio, i.e., chemiluminescence at a particular rRNA concentration divided by chemiluminescence of control.

These data demonstrate that the addition of selective degradation before separation results in lower backgrounds leading to higher signal to background ratios, and therefore improved sensitivity.

EXAMPLE 15

Improved Stringency using Differential Hydrolysis

The following probe was constructed to contain an internal linker-arm, type "X" (position of insertion indicated by # below), labeled with acridinium ester, and purified as described in Example 1:

ATT CCG CAC A#TG TCA AAA CCA G

This probe is exactly complementary to the 16S subunit of *Neisseria gonorrhoeae*. However, it is also closely related to *N. meningitidis*, and a cross-reaction is typically observed under the hybridization stringency conditions cited in Examples 2 and 8. This probe was hybridized with 0.5 µg *N. meningitidis* as described in Example 8, (except in a 200 µl format), then either incubated for 10 minutes at 60° C. in 1 ml of 0.2M sodium tetraborate, pH 7.6, 5% Triton X-100 to effectuate differential hydrolysis (+D.H.), or not subjected to these differential hydrolysis conditions (–D.H.). The resulting hybrids were then separated on magnetic microspheres and measured for chemiluminescence as described below.

Add 1 ml of 0.4M PB, pH 6.0, containing 150 µg of magnetic amine microspheres (BioMag M4100, Advanced Magnetics, Inc., Cambridge, Mass.). Vortex 10 seconds. Incubate at 60° C. for 5 minutes. Vortex 10 seconds. Magnetically separate the spheres from the solution using the Pace-Mate™ magnetic separation rack (Gen-Probe, Inc., San Diego, Calif.). Discard liquid. Wash the spheres by adding 1 ml of 0.3M PB, pH 6.0, vortexing for 10 seconds, magnetically separating and discarding the liquid. Repeat for a total of three washes. Elute the hybrid by adding 300 µl of 0.2M PB, pH 6.0, 50% formamide, vortexing 10 seconds, incubating at 60° C. for 5 minutes, vortexing for 10 seconds, and magnetically separating the spheres from the solution. Transfer the solution to a Clinilumat tube and measure chemiluminescence as described in Example 7.

RESULTS

| Condition | Chemiluminescence* |
|---|---|
| – D.H. | 178,034 |
| + D.H. | 748 |

*Hybrid signal minues control (i.e., no rRNA) signal, given in relative light units (rlu). Signal from the exact target (i.e., *N. gonorrhoeae*) in this format is typically 7–10 × 10 rlu.

In conclusion, application of the differential hydrolysis technique described herein as an additional stringency discrimination step greatly reduces signal from undesired, cross-reacting sequences. In this example cross-reaction of a *N. gonorrhoeae* probe with *N. meningitidis* was lowered greater than 200-fold. The differential hydrolysis step increases sensitivity to unstable hybrids, which are in equilibrium with unhybridized probe, by constantly reducing the chemiluminescence (via hydrolysis) of the probe when it is in the unhybridized form, thus lowering the chemiluminescence due to cross reaction.

EXAMPLE 16

Detection of a Chimeric Target Sequence Associated with Chronic Myelogenous Leukemia using a Probe Internally Labeled with Acridinium Ester A 24 mer probe (sequence given below) with an internal linker-arm, type "X", inserted as indicated was synthesized, labeled with AE and purified as described in Example 1. This probe is complementary to the chimeric mRNA transcript (common break) associated with chronic myelogenous leukemia (CML) and will be called the bcr/abl probe. This chimeric mRNA is a product of the chimeric gens formed by the translocation of a region of the abl gene into a region of another chromosome containing the bcr gene.

Synthetic DNA 60 mer targets representing the breakpoint junction region of the bcr/abl chimeric target, as well as the normal bcr and abl targets in that same region, were synthesized as described in Example 1 (sequences given below). Also, an mRNA target was produced by transcription of a pGEM clone containing a 450 nucleotide segment of the chimeric bcr/abl gene centered around the breakpoint. An mRNA transcript of the same 450 nucleotide segment in the probe sense was also produced as a negative control.

BCR/ABL PROBE SEQUENCE
5'-CCGCTGAAGGGCTTTT*GAACTCTGC-3'
SYNTHETIC TARGET SEQUENCE
BCR/ABL TARGET
5'ACTCAGCCACTGGATTTAAGCAGAGTTCAA
AGCCCTTCAGCGGCCAGTAGCATCTGACT-3'
ABL TARGET
5'-ACTCAGCCACTGGATTTAAGCAGAGTTCAATCT-
GTACTGCACCCTGGAGGTGGATTCCT-3'

The asterisk inserted above denotes a linker-arm insertion site for acridinium ester attachment and the underline indicates abl sequences.

The bcr/abl probe was hybridized with approximately 1 pmol of each of the targets listed above as described in Example 8, and the stability of these hybrids and the unhybridized probe was tested at pH 7.6 as described in Example 7.

RESULTS

|  |  | half-life (min) | ratio* |
|---|---|---|---|
| Targets: | bcr/abl mRNA | 27.7 | 39.6 |
|  | bcr/abl DNA | 15.0 | 21.4 |
| Controls: | probe sense mRNA | 0.7 | 1 |
|  | abl DNA | 0.7 | 1 |
|  | bcr DNA | 0.7 | 1 |
| Unhybridized probe |  | 0.7 | — |

*Target or control half-life divided by unhybridized probe half-life.

These data demonstrate that an AE-labeled probe designated to span the breakpoint junction region of the chimeric bcr/abl mRNA transcript associated with CML was able to discriminate between chimeric target and normal sequences (as well as unhybridized probe) using the HPA technology described herein. This is a demonstration that the method of the invention can be used to specifically detect chimeric targets (typically associated with genetic disorders) in the presence of the normal, non-chimeric component nucleic acids.

This example further demonstrates that targets other than rRNA-in this case both mRNA and DNA—afford protection against AE hydrolysis when hybridized to AE-labeled probe.

We claim:

1. A method for determining the presence or amount of a nucleic acid analyte in a medium comprising the steps of:
    a) providing to said medium a labelled-probe comprising a detectable label and an oligonucleotide able to form a hydrogen-bonded duplex with said analyte, wherein if said analyte is present said labelled-probe forms a hydrogen-bonded labelled-probe:analyte duplex, and if said analyte is not present said labelled-probe is an unbound labelled-probe,
    b) selectively degrading said label present in either said labelled-probe:analyte duplex or in said unbound labelled-probe, such that a signal produced from degraded label is distinct from a signal produced from label not degraded, and
    c) detecting the presence or amount of said label not degraded as a measure of the presence or amount of said nucleic acid analyte in said medium.

2. The method of claim 1, wherein said label present in said unbound labelled-probe is selectively degraded in said step (b).

3. The method of claim 2, wherein said detecting is done by means selected from the group consisting of colorimetric, fluorimetric, chemiluminescent and bioluminescent means.

4. The method of claim 3, wherein said label is a fluorescent or chemiluminescent molecule.

5. The method of claim 4, wherein said label is an acridinium ester or a derivative thereof.

6. The method of claim 5, wherein said label is an acridinium ester.

7. The method of claim 4, wherein said label is detected as chemiluminescence involving attack on an acridinium species forming an electronically excited acridone species.

8. The method of claim 1, further comprising separating said labelled-probe:analyte duplex from said unbound labelled-probe prior to said step (c).

9. The method of claim 7, further comprising separating said labelled-probe:analyte duplex from said unbound labelled-probe prior to said step (c).

* * * * *